United States Patent [19]

Voss et al.

[11] Patent Number: 4,675,050
[45] Date of Patent: Jun. 23, 1987

[54] SULFATE AND SULFONATE BETA-NAPHTHOL POLYGLYCOL ETHERS

[75] Inventors: Günter Voss; Hubert-Matthias Seidenspinner, both of Berlin, Fed. Rep. of Germany

[73] Assignee: Schering AG, Berlin and Bergkamen, Fed. Rep. of Germany

[21] Appl. No.: 774,401

[22] Filed: Sep. 6, 1985

[30] Foreign Application Priority Data

Sep. 6, 1984 [DE] Fed. Rep. of Germany ....... 3432956

[51] Int. Cl.$^4$ ............................................. C23C 16/00
[52] U.S. Cl. .................................. 106/1.17; 106/1.29; 427/433
[58] Field of Search ............................. 106/1.17, 1.29; 427/433

[56] References Cited

U.S. PATENT DOCUMENTS

| | | | |
|---|---|---|---|
| 3,472,743 | 10/1969 | Rushmere | 106/1.29 |
| 4,075,066 | 2/1978 | Eckles et al. | 204/55 R |
| 4,496,439 | 1/1985 | Grief et al. | 204/55 R |

FOREIGN PATENT DOCUMENTS

| | | |
|---|---|---|
| 3248503 | 5/1984 | Fed. Rep. of Germany . |
| 0017091 | 1/1985 | Japan . |

*Primary Examiner*—Paul Lieberman
*Assistant Examiner*—Willie J. Thompson
*Attorney, Agent, or Firm*—Michael J. Striker

[57] ABSTRACT

New surface active compounds are disclosed having the Formula (I)

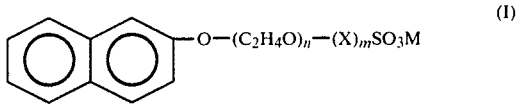

in which
X is an unsubstituted $C_1$ to $C_6$ alkylene group, a $C_1$ to $C_6$ alkylene group substituted by one or more hydroxy, oxo, methyl or carboxy groups, an unsubstituted p-phenylene group, or a p-phenylene group substituted by one or more halo or $C_1$ to $C_4$ alkyl groups;
M is hydrogen or a salt-forming cation;
n is a whole number from 6 to 60; and
m is 0 or 1.

The new surface active compounds are employed in aqueous acid galvanic zinc baths to improve the quality of the resulting zinc coating.

17 Claims, No Drawings

SULFATE AND SULFONATE BETA-NAPHTHOL POLYGLYCOL ETHERS

FIELD OF THE INVENTION

This invention relates to sulfate and sulfonate beta-naphthol polyglycol ethers used as surface active agents. The invention further relates to the addition of the new compounds to acid galvanic zinc baths to obtain a good deposition of zinc on a given substrate.

BACKGROUND OF THE INVENTION

The use of sulfated and/or sulfonated alkyl phenol ethoxylates in acid galvanic zinc baths is known according to DE OS No. 32 48 503. Such baths have the disadvantage that a disturbing foam layer is developed when air is bubbled therethrough, thereby preventing a perfect deposition of zinc on the substrate (e.g. ferrous metal substrate).

The use of polyoxylated naphthols in combination with anionic sulfonic acid condensation products and sulfonic acids, as well as with nonionic sulfonic acid condensation products, is also known from U.S. Pat. No. 4,075,066. These zinc baths have the disadvantage that the turbidity temperature decreases in the course of processing and must then be increased by large doses of selected wetting agents.

OBJECTS OF THE INVENTION

It is an object of the invention to provide new surface active agents which are especially useful in acid galvanic zinc baths.

It is a further object of the invention to provide galvanic acid zinc baths containing the new surface active compounds, said zinc baths having a high turbidity temperature, thus enabling a perfect metal deposition without forming foam.

SUMMARY OF THE INVENTION

These objects are met, according to the invention, by providing sulfate and sulfonate beta-naphthol polyglycol ethers having the Formula (I)

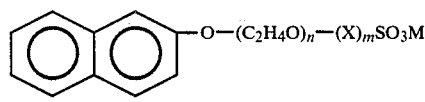
(I)

in which
X is an unsubstituted $C_1$ to $C_6$ alkylene group, a $C_1$ to $C_6$ alkylene group substituted by one or more hydroxy, oxo, methyl or carboxy groups, an unsubstituted p-phenylene group, or a p-phenylene group substituted by one or more halo or $C_1$ to $C_4$ alkyl groups;
M is hydrogen or a salt-forming cation;
n is a whole number from 6 to 60; and
m is 0 or 1.

When the p-phenylene groups are substituted by halo, the halo may be fluoro, chloro, bromo or iodo, preferably chloro. When the p-phenylene groups are substituted by $C_1$ to $C_4$ alkyl, the alkyl group is preferably methyl.

Where M is a salt-forming cation, it is a cation capable of forming a sulfate or sulfonate salt of the Formula (I) that will be effective as a surface active agent in an acid galvanic zinc bath. The preferred cations are the alkali metal cations (e.g. $Li^+$, $Na^+$, $K^+$), the ammonium cations, and the alkali earth metal cations (e.g. $Mg^{2+}$, $Ca^{2+}$, $Ba^{2+}$). Where the salt-forming cation has a valence greater than 1, it is present in an amount chemically equivalent to the available sulfate or sulfonate groups.

One preferred group of compounds of the Formula (I) is the group where n is a whole number from 15 to 24, m is 1, X is a group of the formula

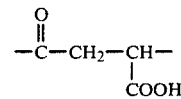

and M is hydrogen, an alkali metal cation, or an ammonium cation. Representative species within this preferred group include:
beta-naphthol polyglycol ether sulfosuccinate with 15 ethylene oxide groups, and
beta-naphthol polyglycol ether sulfosuccinate with 24 ethylene oxide groups.

Another preferred group of compounds of the Formula (I) is that group where n is a whole number from 12 to 24, m is 0, and M is hydrogen, an alkali metal cation, or an ammonium cation. Representative species within this preferred group include:
beta-naphthol polyglycol ether sulfate with 12 ethylene oxide groups, and
beta-naphthol polyglycol ether sulfate with 24 ethylene oxide groups.

The compounds of the Formula (I) are prepared by methods known per se. The compounds of the Formula (I) where m is 0 and n is a whole number from 6 to 60 are prepared by sulfating a beta-naphthol polyglycol ether of the Formula (II)

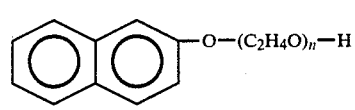
(II)

with sulfuric acid to form the corresponding sulfate ester of the Formula (I). See pp 235 and 336 of *Organic Chemistry*, Brewster, Prentice-Hall, New York, 1948. Instead, chlorosulfonic acid may also be used as sulfating agent.

The compounds of the Formula (I) where m is 1, X is a group of the formula:

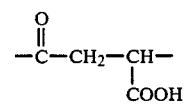

n is a whole number from 6 to 60, preferably 15 to 24, and M is hydrogen, an alkali metal cation, or an ammonium cation, are prepared by esterifying the beta-naphthol polyglycol ether of the Formula (II) with maleic acid or maleic anhydride, followed by reaction with bisulfite or meta-bisulfite to introduce the sulfo group onto the molecule. Again, see p. 235 of *Organic Chemistry*, Brewster, Prentice-Hall, New York 1948.

The following preparation examples show how to prepare the new compounds of the Formula (I):

PREPARATION EXAMPLE 1

Preparation of Beta-naphthol polyglycolether sulfate sodium salt with 12 ethylene oxide groups (4)

1 mole of beta-naphthol polyglycol ether with 12 ethylene oxide groups (1) is dissolved in dioxane. In this solution, under cooling, 1.1 moles of chlorosulfonic acid (2) are stirred, whereby the temperature is not permitted to increase above 30° C.

After addition of the chlorosulfonic acid at about 25°–30° C., the mixture is again stirred for about 3 hours, and then under a partial vacuum, free hydrogen chloride is drawn off by suction.

The remaining sulfate mixture is neutralized with a mixture of about equal parts of ice and NaOH (40° Be) so that the temperature does not exceed 45° C.

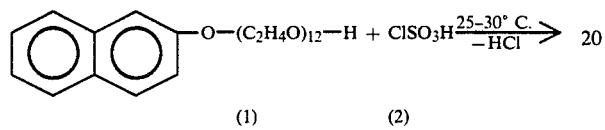

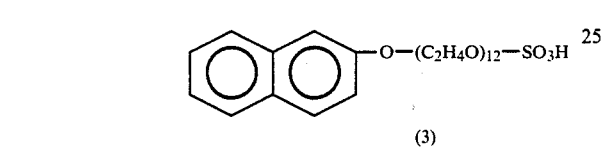

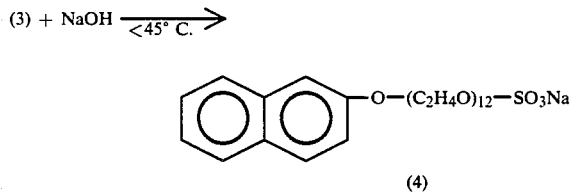

PREPARATION EXAMPLE 2

Preparation of Beta-naphthol polyglycolether sulfate sodium salt with 24 ethylene oxide groups The same procedures and reaction conditions as employed in Preparation Example 1 are employed, except that 1 mole of beta-naphthol-polyglycol ether with 24 ethylene oxide groups is the starting material.

PREPARATION EXAMPLE 3

Preparation of Beta-naphthol polyglycolether sulfosuccinate sodium salt with 24 ethylene oxide groups (4)

1 mole of beta-naphthol polyglycol ether (1) is dissolved in distilled water and in a reaction vessel under a nitrogen atmosphere, the compound is esterified with 1 mole of maleic anhydride (2) with the help of a catalytic amount of amidosulfonic acid at 80° to 100° C. for 4 to 5 hours under elevated pressure.

After the reaction is finished, the solvent medium is distilled off.

The thus formed maleic acid ester (3) is dissolved in a methanol-water solution and mixed with about a 2.5 molar excess of sodium bisulfite (NaHSO₃) and stirred for about 8 to 10 hours at 20° to 25° C.

After this last reaction is terminated, excess sodium bisulfite is filtered off. The filtrate is evaporated under vacuum. As the residue the desired final product is obtained.

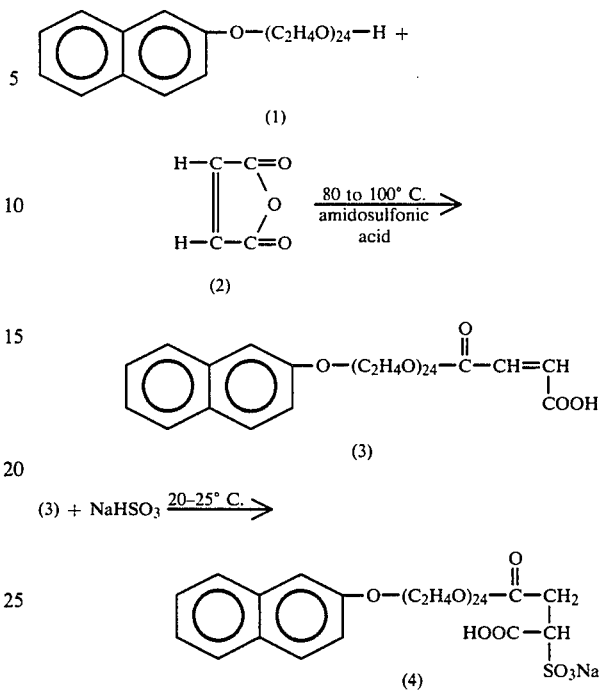

PREPARATION EXAMPLE 4

Preparation of Beta-naphthol polyglycol ether sulfosuccinate sodium salt with 15 ethylene oxide groups The same procedures and reaction conditions as employed in Preparation Example 3 are employed, except that 1 mole of beta-naphthol polyglycol ether with 15 ethylene oxide groups is the starting material.

The compounds of the Formula (I) are distinguished in a surprising manner by an extraordinarily low foam development with simultaneous excellent interfacial action, wherein they are superior to known surface active agents employed under similar conditions in an acid zinc bath.

The compounds of the Formula (I) are particularly suitable as additives to acid zinc baths, which aside from containing all of the conventional ingredients in such a bath, also contain highly effective brighteners. In particular such brighteners as aromatic ketones and aromatic aldehydes, for example, benzal acetone and alpha-chloro-benzaldehyde, are the ones generally utilized in the presence of certain surface active materials due to their low solubility in such baths. The brighteners are added to the bath in an amount ranging from 0.01 to 0.2 g/liter.

The optical brighteners when added to zinc baths, generally form foams, or else have the disadvantage of exerting an unsatisfactory effect in acid zinc baths, which greatly reduces the turbidity temperature of such baths.

The compounds of the Formula (I) overcome the disadvantages of the prior art. Acid zinc baths containing a compound of the Formula (I) do not develop any disturbing foam layer even when air is bubbled through, which makes the new compounds particularly suitable for use in modern high-capacity electrolytes. Other advantages to be emphasized are the stable and high turbidity temperature of the baths, according to the invention, as well as the quality of the metallic coatings deposited from the baths. These coatings are distinguished by brightness as opposed to haziness.

The compounds according to the invention are utilized in quantities of approximately 0.5 to 20 g/liter, preferably 4 to 10 g/liter.

An aqueous solution of zinc chloride and potassium chloride of the following concentrations are generally used as bath solutions:

| zinc chloride (ZnCl₂) | 30–120 g/liter |
|---|---|
| potassium chloride (KCl) | 60–200 g/liter |

Instead of zinc chloride, other zinc salts can also be used, at least in part, such as zinc sulfate, zinc acetate, zinc fluoroborate, and/or zinc sulfamate. Potassium chloride can be partly or entirely replaced by other alkali metal or ammonium salts such as ammonium chloride, ammonium sulfate, or other conducting salts such as sodium chloride, sodium sulfate, or the like. Finally the bath can contain aliphatic and/or aromatic carboxylic acids or their salts such as benzoic acid, salicylic acid, or naphthalenic acid.

Boric acid or other buffers or reagents, as well as nonfoaming wetting agents, can be employed as further additives.

The working conditions are as follows:
pH value: 3.0 to 6.0, preferably 4.5 to 5.5
temperature: 15°–40° C., preferably 20° to 30° C.,
current density: 0.1 to 10.0 A/dm² (cathodic)
Electrolyte movement is carried out, preferably by means of bubbling in air and/or cathode rod movement.

The following examples serve to explain the possibilities for applying the compounds according to the invention:

The examples are carried out in a Hull cell under the conditions stated.

In each instance, an electrolyte solution is used, in which the additives indicated in the examples were dissolved.

EXAMPLE 1

| zinc chloride | 72.0 g/liter |
|---|---|
| potassium chloride | 155.0 g/liter |
| boric acid | 23.0 g/liter |
| benzoic acid | 2.0 g/liter |
| benzal acetone | 0.12 g/liter |

| (a) Additive According to the Present Invention beta-naphthol polyglycol ether sulfosuccinate with 15 ethylene oxide groups | 8.0 g/liter |
|---|---|
| (b) Additive According to U.S. Pat. No. 4,075,066 beta-naphthol polyglycol ether with 15 ethylene oxide groups | 8.0 g/liter |
| (c) Additive According to DE-OS 32 48 503 sulfated nonylphenol polyglycol ether | 8.0 g/liter |

| Execution | |
|---|---|
| cell current | 2A |
| temperature | 22° C. |
| air injection duration: | 10 minutes |

Half of the galvanized sheet iron was then blue chromized.

| Results | | |
|---|---|---|
| (a) | bath solution turbidity temperature high gloss ductile zinc precipitate | does not foam >100° C. |
| (b) | bath solution turbidity temperature high gloss, ductile zinc precipitate with scorching at high current density | does not foam 26.5° C. |
| (c) | bath solution turbidity temperature high gloss, hazed ductile zinc precipitate with scorching at high current density | foams approximately 80° C. |

EXAMPLE 2

| zinc chloride | 72.0 g/liter |
|---|---|
| potassium chloride | 155.0 g/liter |
| boric acid | 23.0 g/liter |
| benzoic acid | 2.0 g/liter |
| benzalacetone | 0.1 g/liter |
| acetophenone | 0.02 g/liter |

| (a) Additive According to the Present Invention beta-naphthol polyglycol ether sulfate with 24 ethylene oxide groups | 8.0 g/liter |
|---|---|
| (b) Additive According to DE-OS 32 48 503 (1) nonyl phenyl polyglycol ether with 14 ethylene oxide groups, and | 4.0 g/liter, |
| (2) sulfated nonylphenol polyglycol ether | 4.0 g/liter |

| Execution | |
|---|---|
| cell current | 2A |
| temperature | 22° C. |
| air injection duration | 10 minutes |

Half of the galvanized sheet iron was then blue chromized.

| Results |
|---|
| (a) bath solution does not foam, turbidity temperature 75° C., high gloss, ductile zinc precipitate |
| (b) bath solution foams considerably, turbidity temperature approximately 71° C., high gloss, hazy, ductile zinc precipitate with dendrite formation in high current density range |

EXAMPLE 3

| zinc chloride | 72.0 g/liter |
|---|---|
| potassium chloride | 155.0 g/liter |
| boric acid | 23.0 g/liter |
| benzoic acid | 0.08 g/liter |
| O—chloro-benzaldehyde | 0.04 g/liter |
| ethyl hexanol polyglycol ether with 15 ethylene oxide groups | 2.0 g/liter |
| cumolsulfonate sodium | 2.0 g/liter |

| (a) Additive According to the Present Invention beta-naphthol polyglycol ether sulfosuccinate with 24 ethylene oxide groups | 4.0 g/liter |
|---|---|
| (b) Known Additive According to U.S. Pat. No. 4,075,066 beta-naphthol polyglycol ether with 15 ethylene oxide groups | 4.0 g/liter |

| Execution | |
|---|---|
| cell current | 2A |
| temperature | 22° C. |
| air injection duration: | 10 minutes |

Half of the galvanized sheet iron was then blue-chromized.

| Results | |
|---|---|
| (a) | bath solution does not foam<br>turbidity temperature 88° C.<br>high gloss, ductile zinc precipitate |
| (b) | bath solution does not foam<br>turbidity temperature 44° C. (dropping)<br>high gloss, hazy, ductile zinc precipitate |

EXAMPLE 4

| zinc chloride | 72.0 g/liter |
|---|---|
| potassium chloride | 155.0 g/liter |
| boric acid | 23.0 g/liter |
| benzoic acid | 2.0 g/liter |
| benzal acetone | 0.03 g/liter |
| O—chlorobenzaldehyde | 0.05 g/liter |
| (a) Additive According to the Invention<br>beta-naphthol polyglycol ether sulfosuccinate<br>with 15 ethylene oxide groups | 8.0 g/liter |

| Execution | |
|---|---|
| cell current | 2A |
| temperature | 22° C. |
| air injection duration: | 10 minutes |

Half of the galvanized sheet iron was then blue chromized.

| Results | |
|---|---|
| (a) | bath solution does not foam<br>turbidity temperature >100° C.<br>high gloss, ductile zinc precipitate |

EXAMPLE 5

| zinc chloride | 72.0 g/liter |
|---|---|
| potassium chloride | 155.0 g/liter |
| boric acid | 23.0 g/liter |
| benzoic acid | 2.0 g/liter |
| benzal acetone | 0.03 g/liter |
| O—chlorobenzaldehyde | 0.05 g/liter |
| (a) Additive According to the Present Invention<br>beta-naphthol polyglycol ether sulfate with 12<br>ethylene oxide groups | 8.0 g/liter |

| Execution | |
|---|---|
| cell current | 2A |
| temperature | 22° C. |
| air injection duration: | 10 minutes |

Half of the galvanized sheet iron was then blue chromized.

| Results |
|---|
| bath solution does not foam<br>turbidity temperature: greater than 100° C.<br>high gloss, ductile zinc precipitate with slight scorching zone. |

What is claimed is:

1. An aqueous acid galvanic acid bath which comprises:
   (a) 30 to 120 g/liter of a zinc salt selected from the group consisting of zinc chloride, zinc sulfate, zinc acetate, zinc fluoroborate, zinc sulfamate, and mixtures thereof;
   (b) 60 to 200 g/liter of an alkali metal or ammonium conducting salt; and
   (c) 0.5 to 20 g/liter of a compound of the Formula (I)

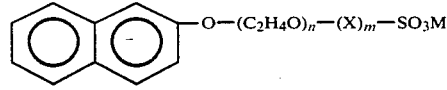

in which
X is an unsubstituted $C_1$ to $C_6$ alkylene group, a $C_1$ to $C_6$ alkylene group substituted by one or more hydroxy, oxo, methyl or carboxy groups, an unsubstituted p-phenylene group, or a p-phenylene group substituted by one or more halo or $C_1$ to $C_4$ alkyl groups;
M is hydrogen or a salt-forming cation;
n is a whole number from 6 to 60; and
m is 0 or 1.

2. The aqueous acid galvanic zinc bath defined in claim 1 which comprises 4 to 10 g/liter of the compound of the Formula (I).

3. The aqueous acid galvanic zinc bath defined in claim 1 which further comprises 0.01 to 0.2 g/liter of a brightener.

4. The aqueous acid galvanic zinc bath defined in claim 3 wherein the brightener is an aromatic ketone or aromatic aldehyde.

5. The aqueous acid galvanic zinc bath defined in claim 1 wherein the compound of the Formula (I) is selected from the group consisting of:
   beta-naphthol-polyglycol ether sulfate with 12 ethylene oxide groups, and
   beta-naphthol-polyglycol ether sulfate with 24 ethylene oxide groups.

6. A method of reducing the surface tension of an aqueous acid galvanic zinc bath which comprises the step of adding to said bath, 0.5 to 20 g/liter of a compound of the Formula (I)

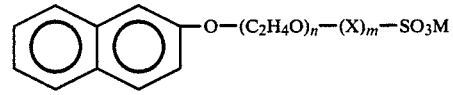

in which
X is an unsubstituted $C_1$ to $C_6$ alkylene group, a $C_1$ to $C_6$ alkylene group substituted by one more hydroxy, oxo, methyl, or carboxy groups, an unsubstituted p-phenylene group, or a p-phenylene group substituted by one or more halo or $C_1$ to $C_4$ alkyl groups;
M is hydrogen or a salt-forming cation;
n is a whole number from 6 to 60; and
m is 0 or 1.

7. An aqueous acid galvanic zinc bath which comprises:
   (a) 30 to 120 g/liter of a zinc salt selected from the group consisting of zinc chloride, zinc sulfate, zinc acetate, zinc fluoroborate, zinc sulfamate, and mixtures thereof;
   (b) 60 to 200 g/liter of an alkali metal or ammonium conducting salt; and (c) 0.5 to 20 g/liter of a compound of the Formula (I)

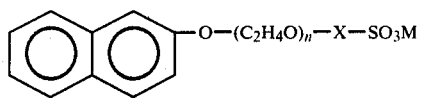

in which
X is an unsubstituted $C_1$ to $C_6$ alkylene group, a $C_1$ to $C_6$ alkylene group substituted by one or more hydroxy, oxo, methyl, or carboxy groups, an unsubstituted p-phenylene group, or a p-phenylene group substituted by one or more halo or $C_1$ to $C_4$ alkyl groups;
M is hydrogen or a salt-forming cation; and
n is a whole number from 6 to 60.

8. The aqueous acid galvanic zinc bath defined in claim 7 which comprises 4 to 10 g/liter of the compound of the Formula (I).

9. The aqueous acid galvanic zinc bath defined in claim 7 which comprises 0.01 to 0.2 g/liter of a brightener.

10. The aqueous acid galvanic zinc bath defined in claim 9 wherein the brightener is an aromatic ketone or aromatic aldehyde.

11. A method of reducing the surface tension of an aqueous acid galvanic zinc bath which comprises the step of adding to said bath, 0.5 to 20 g/liter of a compound of the Formula (I)

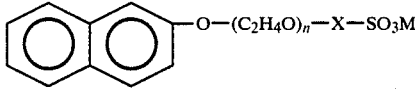

in which
X is an unsubstituted $C_1$ to $C_6$ alkylene group, a $C_1$ to $C_6$ alkylene group substituted by one or more hydroxy, oxo, methyl or carboxy groups, an unsubstituted p-phenylene group, or a p-phenylene group substituted by one or more halo or $C_1$ to $C_4$ alkyl groups;
M is hydrogen or a salt-forming cation; and
n is a whole number from 6 to 60.

12. An aqueous acid galvanic zinc bath which comprises:

(a) 30 to 120 g/liter of a zinc salt selected from the group consisting of zinc chloride, zinc sulfate, zinc acetate, zinc fluoroborate, zinc sulfamate, and mixtures thereof;
(b) 60 to 200 g/liter of an alkali metal or ammonium conducting salt; and
(c) 0.5 to 20 g/liter of a compound of the Formula (I)

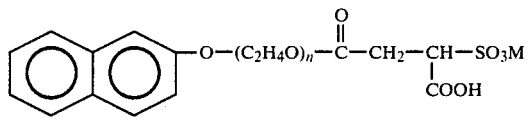

in which
M is hydrogen or a salt-forming cation; and
n is a whole number from 15 to 24.

13. The aqueous acid galvanic zinc bath defined in claim 12 which comprises 4 to 10 g/liter of the compound of the Formula (I).

14. The aqueous acid galvanic zinc bath defined in claim 12 which further comprises 0.01 to 0.2 g/liter of a brightener.

15. The aqueous acid galvanic zinc bath defined in claim 14 wherein the brightener is an aromatic ketone or aromatic aldehyde.

16. The aqueous acid galvanic zinc bath defined in claim 12 wherein the compound of the Formula (I) is selected from the group consisting of:
beta-naphthol polyglycol ether-sulfosuccinate with 15 ethylene oxide groups; and
beta-naphthol polyglycol ether-sulfosuccinate with 24 ethylene oxide groups.

17. A method of reducing the surface tension of an aqueous acid galvanic zinc bath which comprises the step of adding to said bath, 0.5 to 20 g/liter of a compound of the Formula (I)

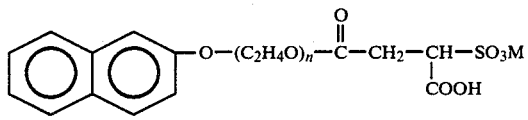

in which
M is hydrogen or a salt-forming cation; and
n is a whole number from 15 to 24.

* * * * *